US00PP09027P

United States Patent [19]

Hoff

[11] Patent Number: Plant 9,027

[45] Date of Patent: Jan. 3, 1995

[54] VARIETY OF LILIUM NAMED ZSAZSA

[75] Inventor: Petrus M. M. Hoff, Steenbergen, Netherlands

[73] Assignee: Hoffgaarde B.V., Steenbergen, Netherlands

[21] Appl. No.: 177,194

[22] Filed: Jan. 4, 1994

[51] Int. Cl.[6] ..... A01H 5/00

[52] U.S. Cl. ..... Plt./87.4

[58] Field of Search ..... Plt. 87.4

[56] References Cited

U.S. PATENT DOCUMENTS

PP7274 7/1990 Van der Salm ..... Plt./87.4

*Primary Examiner*—James R. Feyrer

*Attorney, Agent, or Firm*—Webb Ziesenheim Bruening Logsdon Orkin & Hanson

[57] ABSTRACT

A new and distinct cultivar of lily plant named Zsazsa, particularly characterized by greenish ivory flowers, height of about 120 cm, pedicel of 10–12 cm in length with 2–4 flowers, rather large, impressive leaves, occasional bulblets, and capable of producing stems and flowers for cut-flower production.

1 Drawing Sheet

BACKGROUND OF THE INVENTION

The present invention comprises a new and distinct cultivar of lily, botanically known as Lilium asiatic and hereinafter referred to by the cultivar name Zsazsa.

The new cultivar is a product of a planned breeding program which had the objectives of creating new lily cultivars with the capacity to produce stems and flowers for cut-flower production.

The new cultivar was originated from a hybridization made by the inventor Messr. Petrus Mattheus Maria Hoff in a controlled breeding program at Hoffgaarde, B.V., Franseweg 9, 4651 PV Steenbergen, The Netherlands in 1989. The female and male parents were seedlings originated by Applicant, which were proprietary, and maintained by Applicant for breeding purposes.

The new cultivar was discovered and selected as one flowering plant within the progeny of the stated cross by the inventor on May 30, 1991 in a controlled environment in Steenbergen.

The first act of asexual reproduction of the new cultivar was accomplished by the inventor when scales were taken from the initial selection on Oct. 31, 1991 in a controlled environment in Steenbergen.

Horticultural examination of selected units initiated Apr. 1, 1992 has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light, intensity, and day length. The following observations, measurements, and comparisons describe plants grown in Steenbergen under greenhouse conditions which approximate those generally used in commercial practice. The following traits have been repeatedly observed and are determined to be basic characteristics of the new cultivar which in combination distinguish this lily as a new and distinct cultivar.

1) Color of the flowers (greenish ivory).

2) About 12 cm in height from soil surface to top of the plant.

3) Pedicel 10–12 cm in length with 2–4 flowers.

4) Rather large, impressive leaves.

5) Occasional bulblets on upper 40% of the stem including the crown.

The accompanying color photographic drawing shows typically flower characteristics of the new cultivar, with colors being as true as possible with illustrations of this type. In the following description, color references are made to The Royal Horticultural Society Colour Chart. The color values were determined at Steenbergen on Apr. 1, 1992.

THE PLANT

Classification:

*Botanic.*—*Lilium asiatic.*

*Commercial.*—Hybrid asiatic lily for cut flower production.

Form: Single upright stem from each bulb.

Height: About 120 cm.

Growth habit: Upright, erect, strong and vigorous.

Stem:

*Diameter.*—1.2 cm average.

*Form.*—Rounded.

*Color.*—Yellow-Green Group 146A.

Foilage:

*Quantity.*—150–175 leaves.

*Size of leaf.*—About 12 cm long, 1.3 cm wide up to about 16 cm long, 2.4 cm wide.

*Shape of leaf.*—Narrow oblong.

*Texture of leaf.*—Smooth.

*Color.*—Green Group 138A.

Bulbs:

*Size.*—12–14 cm in circumference.

*Color.*—White.

THE BUD

Form: Rounded ends (UPOV Type II).
Size: 10 cm in length.
Color: Yellow-Green Group 150A.

THE FLOWER

Blooming habit: 110 days after planting.
Size: 20 cm in diameter.
Borne: Umbellate, single.
Shape: Narrow, acute (UPOV Type VIII).
Tepalage:

*Number of tepals.*—6.

*Arrangement.*—Hexagonal, inner tepals about 1 cm apart at their bases.

*Size.*—12–13 cm long; inner tepals 4–5 cm wide; outer tepals 2.5–3.5 cm wide.

*Color (inner and outer tepals).*—Upper surface: Green-White Group 157A at the apex, becoming progressively more Yellow-Green Group 145D at the base with occasional Yellow Group 11B. Lower surface: Green-White Group 157A.

*Spotting.*—Very few on outer tepals, more on inner tepals, 1–1.5 mm wide, located in a scattered ring at the base of the tepals.

*Reflexing.*—None.

Pedicel:

*Length.*—10–12 cm.

*Color.*—Light green.

*Form.*—Upright.

Texture: Rough.
Nectaries (size): 2–3 cm.
Disease resistance: No unusual disease problems have ben observed.
Fragrance: None.
Lasting quality: 14 days in water after cutting.

REPRODUCTIVE ORGANS

Stamens:

*Number.*—6.

*Length.*—9 cm.

*Anthers-color.*—Reddish-brown.

*Pollen-color.*—Greyed-Orange Group 165B.

*Filaments-color.*—Yellow Group 4D.

Pistils: One, long.
Stigma

*Color.*—Greyed-Orange Group 165A.

Ovaries

*Color.*—Yellow Group 4D.

I claim:

1. A new and distinct variety of lily plant substantially as shown and described.

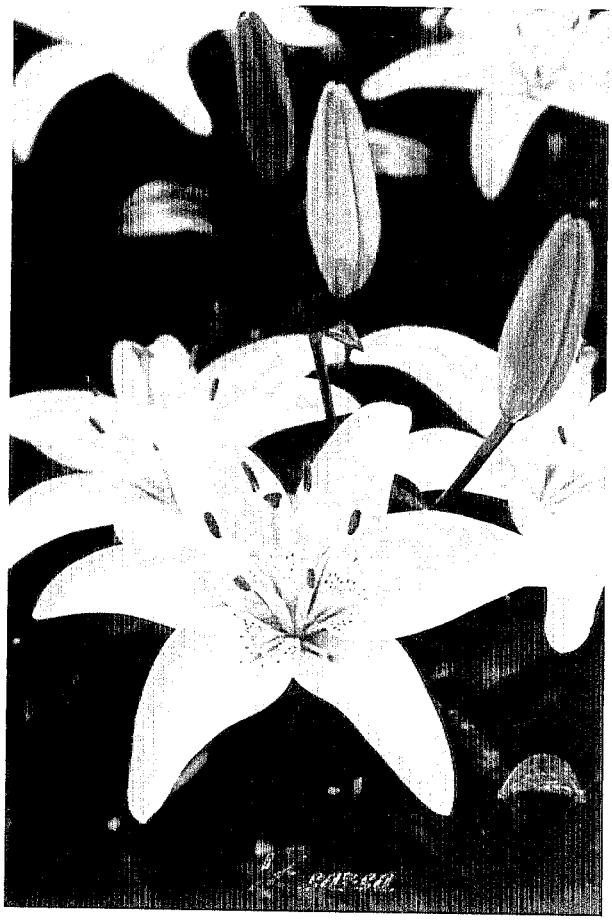

* * * * *